United States Patent
Henschel et al.

(10) Patent No.: US 9,579,511 B2
(45) Date of Patent: Feb. 28, 2017

(54) MEDICAL DEVICE WITH SURFACE MOUNTED LEAD CONNECTOR

(71) Applicant: Medtronic, Inc., Minneapolis, MN (US)

(72) Inventors: Mark E. Henschel, Phoenix, AZ (US); Songhua Shi, Chandler, AZ (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/570,531

(22) Filed: Dec. 15, 2014

(65) Prior Publication Data
US 2016/0166825 A1      Jun. 16, 2016

(51) Int. Cl.
| | | |
|---|---|---|
| A61N 1/375 | (2006.01) | |
| A61N 1/04 | (2006.01) | |
| A61N 1/36 | (2006.01) | |
| A61N 1/362 | (2006.01) | |
| H01R 13/52 | (2006.01) | |
| A61N 1/05 | (2006.01) | |

(52) U.S. Cl.
CPC .......... *A61N 1/3752* (2013.01); *A61N 1/0456* (2013.01); *A61N 1/0472* (2013.01); *A61N 1/0595* (2013.01); *A61N 1/36017* (2013.01); *A61N 1/3625* (2013.01); *H01R 13/5224* (2013.01); *H01R 2201/12* (2013.01)

(58) Field of Classification Search
None
See application file for complete search history.

(56) References Cited

U.S. PATENT DOCUMENTS

| | | | | |
|---|---|---|---|---|
| 4,898,173 A | * | 2/1990 | Daglow | A61N 1/3752 439/585 |
| 5,223,672 A | * | 6/1993 | Pinneo | B23K 20/129 156/73.5 |
| 5,782,891 A | * | 7/1998 | Hassler | A61N 1/3754 607/36 |
| 5,814,090 A | * | 9/1998 | Latterell | A61N 1/375 607/36 |

(Continued)

OTHER PUBLICATIONS

Polyvinyl Chloride (PVC) Datasheet, Copyright 2013, polymerisation.org [retrieved on Apr. 17, 2015]. Retrieved from the Internet: <URL:http://polymerisation.org/polyvinyl-chloride-pvc/>; 2 pgs.

*Primary Examiner* — Kennedy Schaetzle

(57) ABSTRACT

A medical device includes a printed circuit board, a connector mounted on the printed circuit board, and a polymeric body molded over the connector and the printed circuit board. The connector is configured to receive a medical lead and electrically and mechanically couple the lead to the printed circuit board. The connector comprises a housing and feedthrough assembly that includes a polymeric housing and a conductor. The housing defines a bore configured to receive the lead and defines a feedthrough opening through which the conductor extends. The housing and feedthrough assembly is sealed except for an aperture in communication with the bore. The connector further includes a contact disposed in the bore. The conductor electrically couples the contact with the printed circuit board. When a lead is properly received by the bore, the contact couples the lead to the printed circuit board via the conductor.

15 Claims, 9 Drawing Sheets

(56) References Cited

U.S. PATENT DOCUMENTS

| | | | |
|---|---|---|---|
| 6,192,277 B1* | 2/2001 | Lim | A61N 1/3752 607/37 |
| 6,285,551 B1 | 9/2001 | Brandenburg et al. | |
| 6,824,321 B2 | 11/2004 | Ward et al. | |
| 6,927,482 B1 | 8/2005 | Kim et al. | |
| 7,134,194 B2 | 11/2006 | Brandenburg et al. | |
| 7,189,296 B2 | 3/2007 | Peuramäki | |
| 7,199,438 B2 | 4/2007 | Appelt et al. | |
| 7,242,982 B2* | 7/2007 | Singhal | A61N 1/3605 607/36 |
| 7,254,443 B2 | 8/2007 | Jelen et al. | |
| 7,291,034 B2 | 11/2007 | Wu | |
| 7,337,659 B2 | 3/2008 | Naidu et al. | |
| 7,473,585 B2 | 1/2009 | Brandenburg et al. | |
| 7,616,448 B2 | 11/2009 | Degenkolb et al. | |
| 7,736,191 B1* | 6/2010 | Sochor | A61N 1/3752 439/668 |
| 7,794,256 B1* | 9/2010 | Sochor | H01R 13/025 439/289 |
| 8,058,714 B2 | 11/2011 | Noll et al. | |
| 8,162,684 B1* | 4/2012 | Sochor | A61N 1/3754 439/289 |
| 8,230,575 B2 | 7/2012 | Veenstra et al. | |
| 8,264,074 B2 | 9/2012 | Kim et al. | |
| 8,267,708 B1* | 9/2012 | Sochor | A61N 1/3754 439/289 |
| 8,355,785 B1* | 1/2013 | Hammond | A61N 1/3752 607/37 |
| 8,496,377 B2 | 7/2013 | Harr et al. | |
| 8,555,493 B2 | 10/2013 | Xu et al. | |
| 8,643,169 B2 | 2/2014 | Yow et al. | |
| 2004/0106964 A1* | 6/2004 | Fischer, Sr. | A61N 1/05 607/36 |
| 2004/0116976 A1* | 6/2004 | Spadgenske | A61N 1/3752 607/37 |
| 2004/0215280 A1* | 10/2004 | Dublin | A61N 1/375 607/36 |
| 2004/0215281 A1* | 10/2004 | O'Phelan | A61N 1/3754 607/36 |
| 2006/0030893 A1* | 2/2006 | Laske | A61N 1/375 607/37 |
| 2006/0241715 A1* | 10/2006 | Sprain | A61N 1/375 607/37 |
| 2007/0090321 A1* | 4/2007 | Bork | A61M 5/16881 251/335.2 |
| 2007/0232119 A1* | 10/2007 | Sprain | A61N 1/3754 439/357 |
| 2008/0033500 A1* | 2/2008 | Strother | A61N 1/375 607/36 |
| 2008/0050651 A1 | 2/2008 | Wakai et al. | |
| 2008/0246231 A1* | 10/2008 | Sjostedt | A61N 1/05 277/641 |
| 2008/0315396 A1 | 12/2008 | Kuhlman et al. | |
| 2009/0017668 A1* | 1/2009 | Deininger | H01R 12/592 439/346 |
| 2009/0035454 A1* | 2/2009 | Fjelstad | H05K 1/185 427/96.2 |
| 2010/0154917 A1 | 6/2010 | Batallas et al. | |
| 2010/0198303 A1* | 8/2010 | Haller | A61N 1/36032 607/57 |
| 2010/0240253 A1* | 9/2010 | Kast | A61N 1/3752 439/589 |
| 2011/0036174 A1 | 2/2011 | Hooper et al. | |
| 2011/0037157 A1 | 2/2011 | Shin et al. | |
| 2011/0240166 A1 | 10/2011 | Collier et al. | |
| 2011/0261543 A1 | 10/2011 | Xu et al. | |
| 2014/0033814 A1 | 2/2014 | Wen et al. | |
| 2014/0163646 A1 | 6/2014 | Tischendorf et al. | |
| 2014/0194964 A1* | 7/2014 | Woods | A61N 1/3754 607/119 |
| 2014/0277234 A1* | 9/2014 | O'Flynn | A61N 1/0587 607/17 |
| 2015/0357749 A1* | 12/2015 | Brunner | A61N 1/3752 361/752 |

* cited by examiner

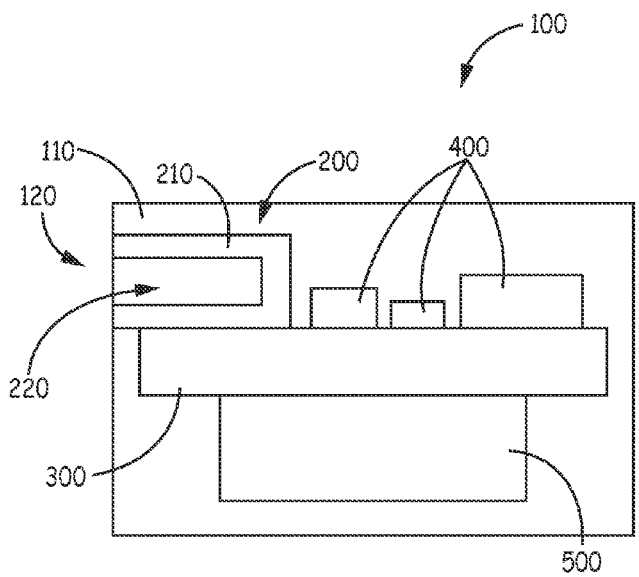
FIG. 4C
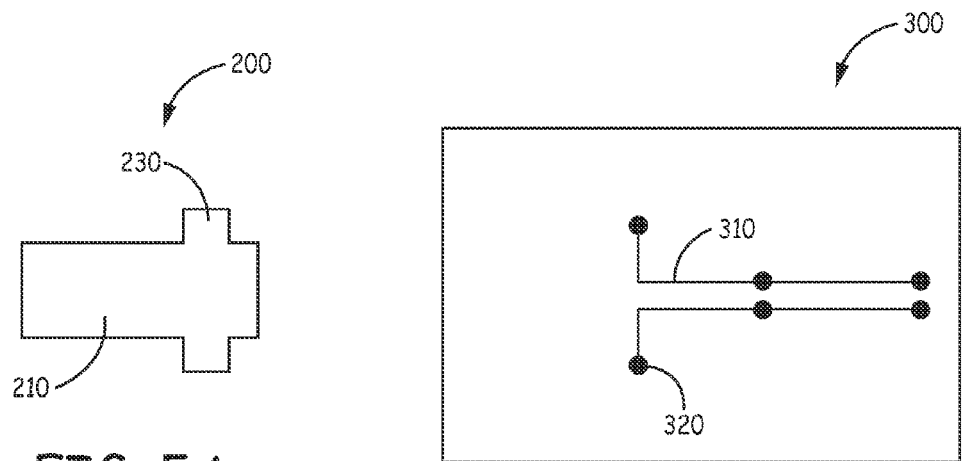
FIG. 5A
FIG. 5B

MEDICAL DEVICE WITH SURFACE MOUNTED LEAD CONNECTOR

FIELD

This disclosure generally relates to, among other things, medical devices having a connector for coupling a medical lead, and methods of manufacture thereof.

BACKGROUND

Implantable medical devices have been developed to have extended lives, and as a result can be expensive to manufacture. For example, lead connectors of implantable medical devices can be formed from materials including, for example titanium, glass, and thermoplastic urethane. Hermetic feedthroughs are often used to couple device electronics to electrical contacts of the lead connector.

Often device manufactures attempt to build on prior platforms to develop new devices. For example, a manufacturer may employ various aspects of a design of a lead connector of an implantable medical device in a lead connector for an external medical device. However, such devices may not need to be built to the same tolerances as long-term implantable medical devices. Accordingly, alternative methods for manufacturing external medical device, particularly those for short-term use could be desirable.

SUMMARY

In various embodiments, this disclosure describes, among other things, medical devices and methods of manufacturing the medical devices. The devices can be short-term external use medical devices. However, in some embodiments, the devices can be longer-term use external medical devices. In some embodiments, the devices can be implantable medical devices.

The devices described herein include a lead connector mounted to a printed circuit board. The connector has a housing defining a bore configured to receive a lead. The connector also includes contacts electrically coupled to the printed circuit board. When the lead is properly inserted into the bore the contacts of the connector electrically couple the lead to the printed circuit board. The printed circuit board and mounted connector are over-molded with a polymer.

The methods described herein include mounting a lead connector to a printed circuit board. The lead connector comprises a housing configured to prevent ingress of polymer into a bore of the housing during an over-molding process. In other words, the housing is sealed relative to the polymer during the over-molding process. During the over-molding process, the bore or an aperture in communication with the bore can be plugged.

In various embodiments described herein, a medical device includes a printed circuit board, a connector mounted on the printed circuit board, and a polymeric body molded over the connector and the printed circuit board. The connector is configured to receive a medical lead and electrically and mechanically couple the lead to the printed circuit board. The connector comprises of a housing and feedthrough assembly that includes a polymeric housing and a conductor. The housing defines a bore configured to receive the lead and defines a feedthrough opening through which the conductor extends. The housing and feedthrough assembly is sealed except for an aperture in communication with the bore. The connector further includes a contact disposed in the bore. The conductor electrically couples the contact with the printed circuit board. When a lead is properly received by the bore, the contact couples the lead to the printed circuit board via the conductor.

In some embodiments, the contact and the conductor comprise a contiguous electrically conductive element, or in other words are formed from a single part. In some embodiments, the feedthrough opening is configured to receive the conductor via interference fit. In some embodiments, the connector further comprises tabs retained relative to the housing. The connector can be mounted to the printed circuit board via the tabs.

In some embodiments, the housing comprises one or more parts. In some embodiments, the housing comprises at least two parts joined by an adhesive. In some embodiments, the housing comprises at least two parts joined by welding. In some embodiments, the housing comprises at least two parts that together define a seam having a sufficiently small width or height and sufficiently large length to prevent the polymer of the polymer body from entering the bore of the housing through the seam when the polymer of the polymer body is over-molded over the connector. In some embodiments, the housing is formed from a single part. For example, the housing can be molded around the conductor and the contact.

In some embodiments, the device further comprises a battery operably coupled to the printed circuit board. The polymeric body can be molded over the connector, block, printed circuit, and the battery. The polymeric body comprises a polymer in contact with the battery. The polymer in contact with the battery can have a molding temperature of less than 250° C., such as less than 200° C., or less than 150° C. In some embodiments, the polymer in contact with the battery comprises polyamide.

In various embodiments described herein, a connector is configured to receive a medical lead and to electrically couple the lead with electronics of a medical device. The connector includes a housing and feedthrough assembly. The housing and feedthrough assembly includes (a) a polymeric housing defining a bore configured to receive the lead, a lead opening in communication with the bore, and a feedthrough opening; and (b) a conductor extending through the feedthrough opening. The conductor is configured to electrically couple to the electronics of the medical device. The housing and feedthrough assembly is sealed except for the opening in communication with the bore. The connector further includes a contact disposed in the bore, electrically coupled to the conductor, and configured to electrically couple to the lead.

In some embodiments, the contact and the conductor comprise a contiguous electrically conductive element, or in other words are formed from a single part. In some embodiments, the feedthrough opening is configured to receive the conductor via interference fit. In some embodiments, the connector further comprises tabs retained relative to the housing. The connector can be mounted to the printed circuit board via the tabs.

One or more embodiments of the devices, systems and methods described herein can have one or more advantages relative to prior devices, systems and methods for coupling a lead to a medical device. Those of skill in the art, upon reading the present disclosure and accompanying drawings, will readily appreciate these advantages.

BRIEF DESCRIPTION OF THE DRAWINGS

FIGS. 4A-C are schematic drawings of a perspective view (4A) and cross-sectional taken through line B-B (4B) and line C-C (4C) of FIG. 4A illustrating an embodiment of a medical device.

FIGS. 5A-D are schematic top views an embodiment of a connector (5A), a printed circuit board (5B), the connector mounted on the printed circuit board (5C), and electronic components and the connector mounted on the printed circuit board (5D) are shown.

Figure 1:
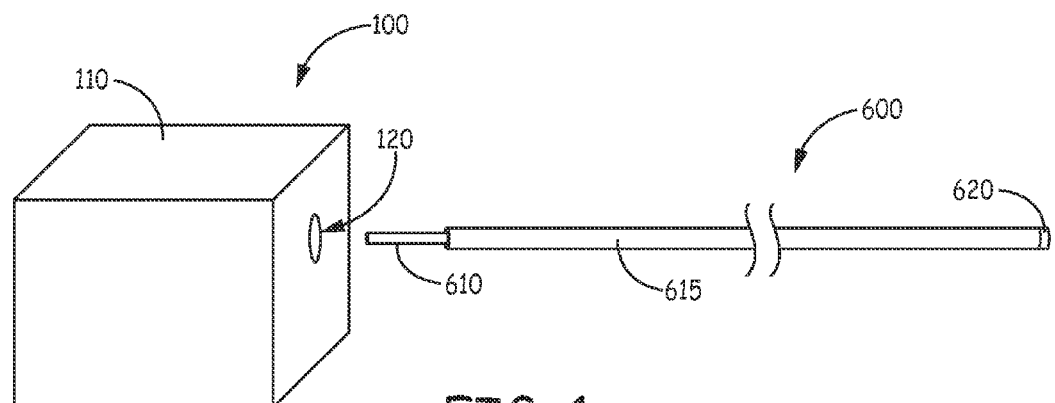
FIG. 1 is a schematic perspective view of an embodiment of a medical device and an embodiment of a medical lead configured to be operably coupled with the medical device.

The schematic drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description several specific embodiments of devices, systems and methods are disclosed. It is to be understood that other embodiments are contemplated and may be made without departing from the scope or spirit of the present disclosure. The following detailed description, therefore, is not to be taken in a limiting sense.

This disclosure relates generally to, among other things, methods, medical devices having a connector for coupling a medical lead, and methods of manufacture thereof. The devices described herein include a lead connector mounted to a printed circuit board in which the printed circuit board and mounted connector are over-molded with a polymer. The lead connector is shrouded with a housing to prevent ingress of polymer into a bore of the connector during an over-molding process.

Any suitable medical device that operably coupled to a lead can be made in accordance with the teachings presented herein. A medical device as described herein can be a therapy delivery device, a monitoring device, or both a therapy delivery device and a monitoring device. For example and with reference to FIG. 1, a schematic perspective view of a medical device 100 and lead 600 are shown. The device 100 has a polymeric body 110 defining an opening 120 configured to receive the lead 600. More particularly, the device 100 is configured to receive through the opening 120 a proximal portion of the lead having a contact 610. When the lead 600 is properly inserted into the device 100, the contact 610 electrically couples with internal electronics (not shown in FIG. 1) of the device 100.

The contact 610 is electrically coupled to an electrode 620 at a distal portion of the lead. A conductor (not shown) extends through lead body 615 from the contact 610 to the electrode 620 and electrically couples the contact 610 to the electrode 620. Electrode 620 can send signals from a patient to electronics of the device or deliver signals generated by the device to the patient. The electrode 620 can be placed in any suitable location to send or receive electrical signals to a patient. For example, the electrode 620 can be placed in external contact with the patient's skin or can be implanted within the patient.

While the lead 600 in FIG. 1 is shown as having only one contact 610 and only one electrode 620, a lead for use with devices described herein can have any suitable number of electrodes and contacts. In some embodiments, the number or contacts and the number of electrodes of a lead are the same. While the device 100 in FIG. 1 is shown as having only one opening 120 configured to receive a lead, a device as described herein can have any suitable number of openings and can be configured to receive any suitable number of leads.

Figure 2:
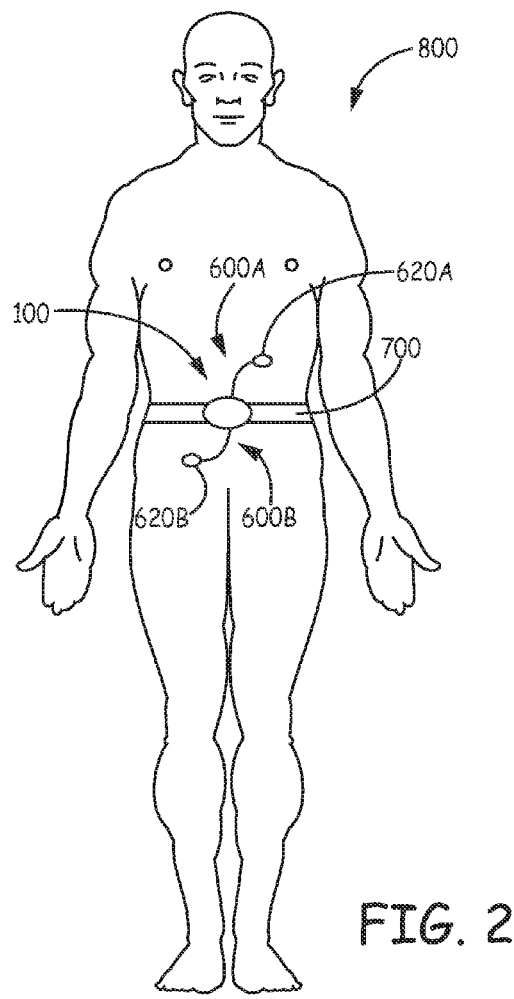
FIG. 2 is a schematic view of a patient wearing an embodiment of a medical device and an embodiment of associated leads.

In some embodiments, the device is an external medical device. In some embodiments, the external medical device is a wearable device. For example and with reference to FIG. 2, a wearable medical device 100 is attached to patient 800 via strap 700, such as a belt or band worn around an appendage or body of the patient. Of course, any suitable method of fixing the device 100 relative to patient 800 can be employed, such as adhesive, adhesive strips, and the like. The depicted system includes two leads 600A, 600B operably coupled to the wearable medical device 100. It will be understood that any suitable number of leads may be operably coupled with a device as described herein. The depicted leads 600A, 600B each have one or more electrodes (one each is depicted) 620A, 620B, respectively, for delivering electrical signals to, or receiving electrical signals from, the patient 800. Each of the electrodes 600A, 600B, independently, can be implanted or in contact with skin of the patient 800.

Any suitable wearable medical device can be made in accordance with the teachings presented herein. For example, the wearable medical device can be a glucose monitoring device, an external pacemaker device, an external neurostimulation device, and the like.

Figure 3:
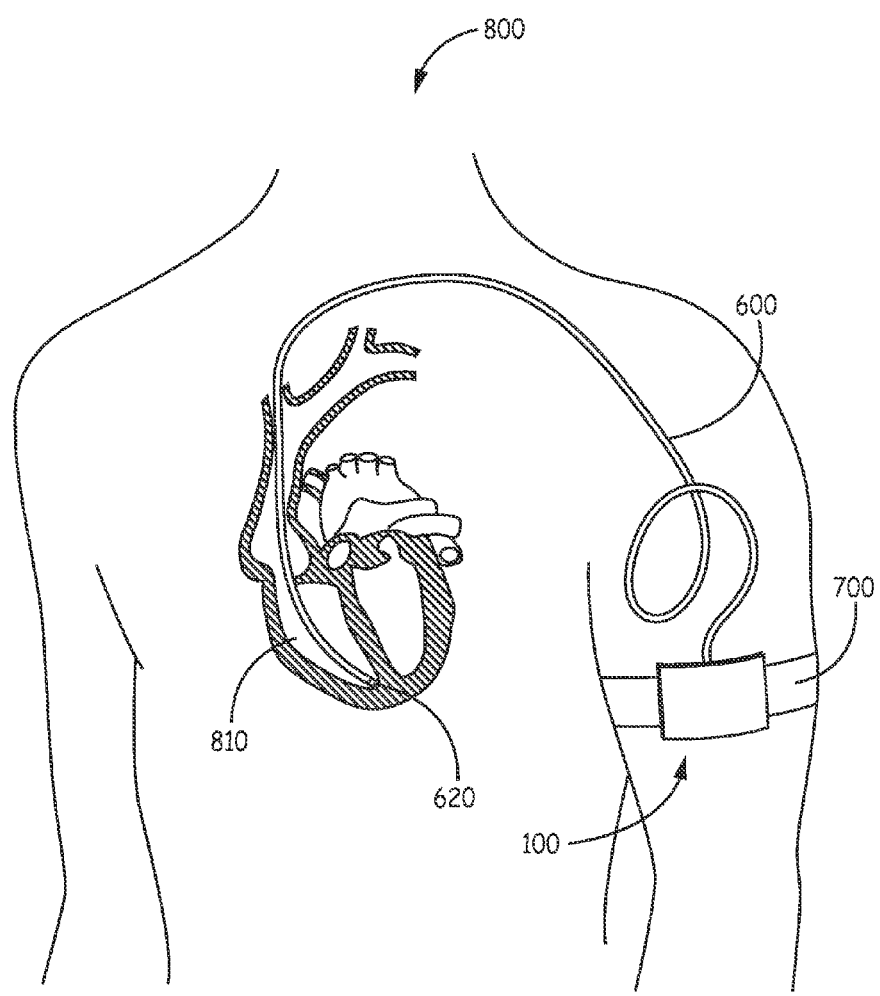
FIG. 3 is a schematic view of a patient wearing an embodiment of a medical device and an embodiment of a lead having a distal portion implanted in the patient's heart.

Referring now to FIG. 3, a medical device 100 anchored by strap 700 to an arm of a patient 800 is depicted. A lead 600 is operably coupled to the medical device 100 and includes an electrode 620 implanted in the patient's heart 810. Such a device 100 can be, for example, a temporary external pacemaker device. As discussed above, the device can be configured to be operably coupled with any suitable number of leads, and each lead can have any suitable number of electrodes.

In some embodiments, the device is an implantable medical device.

Figure 4A:
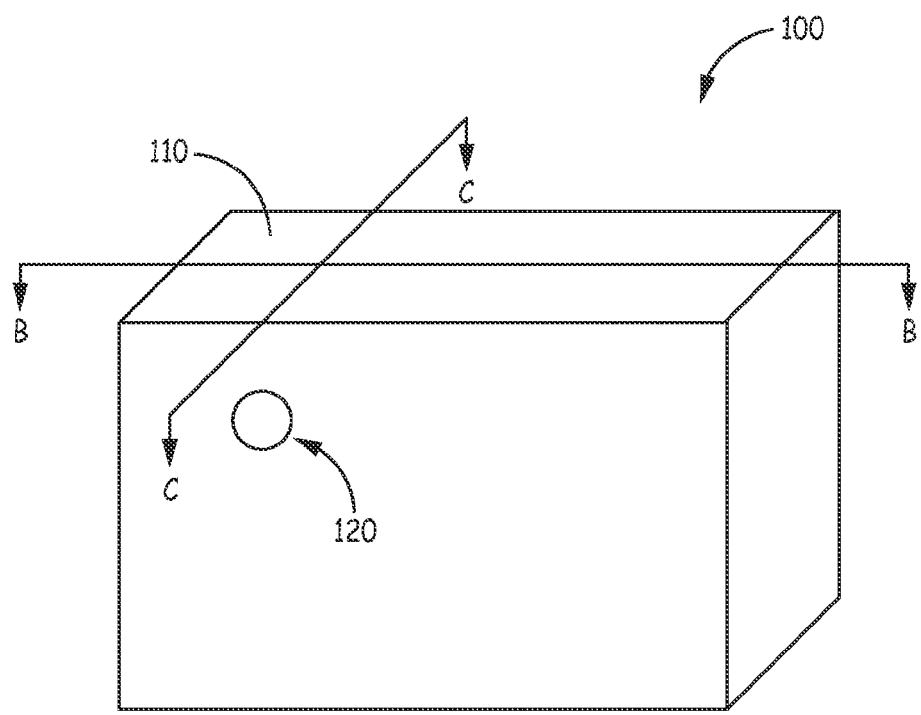
Figure 4B:
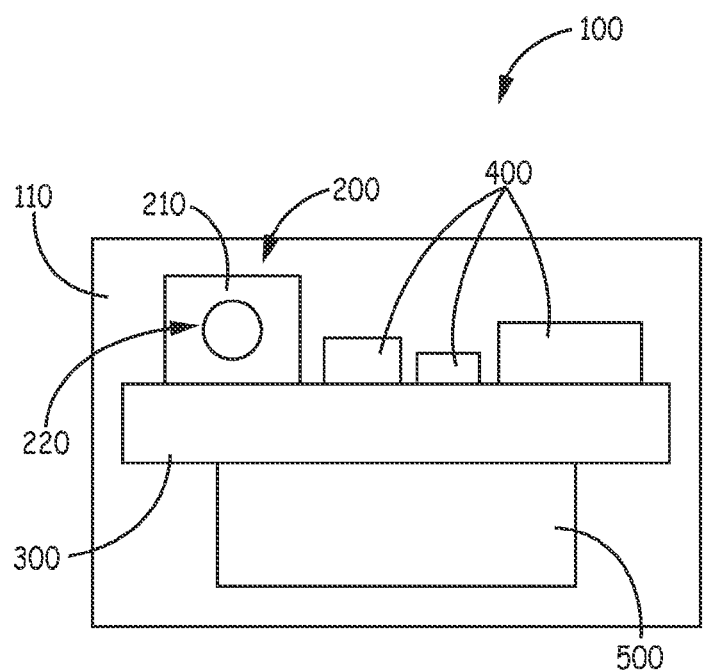

Referring now to FIGS. 4A-C in which a schematic perspective view (FIG. 4A) and schematic cross-sectional views (FIGS. 4B-C) of an embodiment of a medical device 100 are shown. FIG. 4B depicts a section taken through line B-B of FIG. 4A. FIG. 4C depicts a section taken through line CC of FIG. 4A. The device 100, which can be an implantable medical device or an external medical device, such an ambulatory medical device, as described above, includes a polymeric housing 110 that defines an opening 120 configured to receive a medical lead. Opening 120 is in communication with bore 220 defined by housing 210 of lead connector 200. Bore 220 is configured to receive the medical lead. Connector 200 is mounted on printed circuit board 300. Various electronic components 400 are operably coupled to printed circuit board 300 Components 400 are depicted as being mounted on the printed circuit board 300. However, one or more components 400 may be embedded within the printed circuit board 300. In some embodiments, one or more component 400 is mounted on the printed circuit board 300 and one or more components 400 are embedded in the printed circuit board 300. Battery 500 is operably coupled to, and mounted on, printed circuit board 300 to supply electrical power to one or more of the electronic components 400 based on the design of the circuits and components. While not shown, it will be understood that device 100 may include a power source other than battery 500. For example, the device can be a passive device that employs near field communication (NFC); e.g. contains a NFC antenna, to power the device.

Printed circuit board 300 can be formed from any suitable material. For example, the printed circuit board may include a fiberglass-epoxy laminate such as FR-4, a Teflon substrate, a ceramic substrate, a polyimide flexible substrate, or the like. The printed circuit board 300 can include conductor traces applied on the substrate material to form a desired pattern based on a circuit design. The conducting traces can be formed on the substrate material by chemical deposition, etching, lithography, spray deposition, cutting, or the like.

The one or more electronic components 400 can be electrically active or passive components adapted to perform signal generation, modification, analysis or the like to provide electrical therapy to a patient (via an electrode of a lead operably coupled to the device) or to monitor signals received from the patient (via an electrode of a lead operably coupled to the device). Examples of electronic components 400 that can be mounted on or embedded in printed circuit board 300 include integrated circuits, diodes, amplifiers, transistors, oscillators, resistors, capacitors, inductors, transformers, RE transmitter/receiver, interconnects, and the like. The electronic components 400 can perform one or more intended operations associated with the medical device 100. The electronic components 400 can be electrically coupled to conducting traces the printed circuit board 300 in any suitable manner. For example, the components can be coupled to traces using through-hole technology or surface mount technology.

Figure 5C:
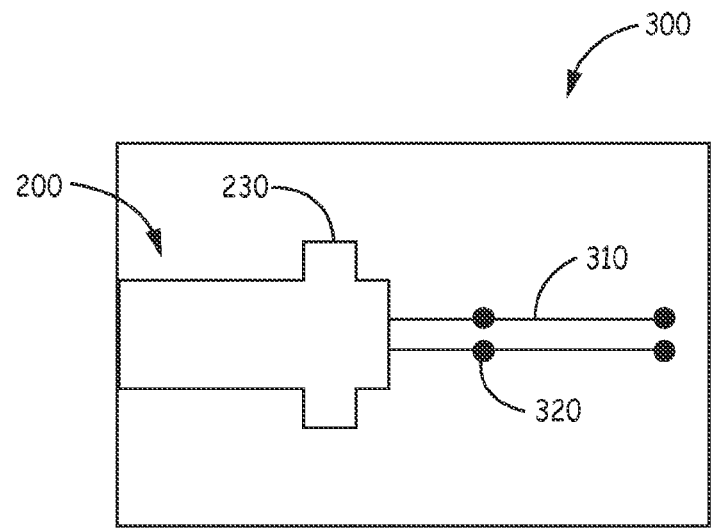
Figure 5D:
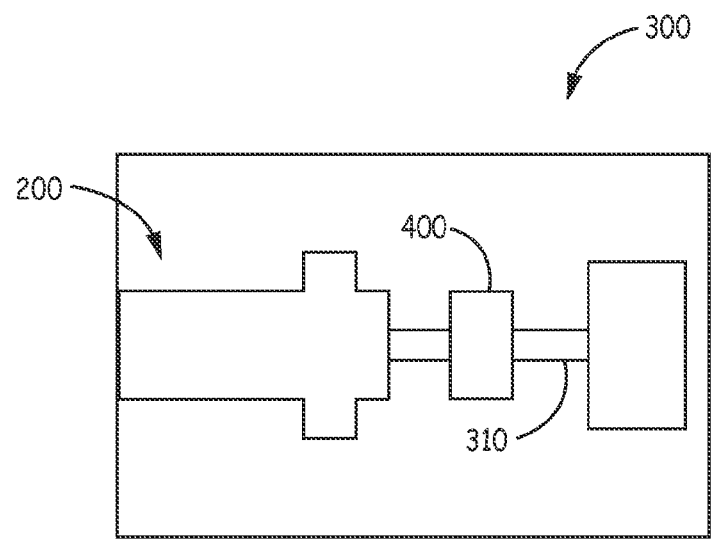

Referring now to FIGS. 5A-D, schematic drawings of an embodiment of lead connector 200, printed circuit board 300 and electronic components 400 and connector 200 mounted to printed circuit board 300 are shown. The depicted connector has tabs or extensions 230 configured to mount the connector 200 to the printed circuit board. The tabs 230 can be conductive and can be electrically coupled to a contact within a lead receptacle bore. Alternatively, the tabs 230 can define one or more feedthrough openings through which conductors that are electrically coupled to one or more contacts within the lead receptacle bore. In some embodiments, one or more conductors (not shown) that are electrically coupled to a contact within the lead receptacle bore exit housing 210 of the connector 200 through a feedthrough opening that is not located at a tab 230. The tabs, if conductive, or conductors can be electrically coupled to one or more traces 310 of the printed circuit board 300 via contacts 320. In the embodiment depicted in FIG. 5C, the tabs 230 of the connector 200 are over two contacts 320 of printed circuit board (compare FIG. 5C with FIGS. 5A and 5B) and can be electrically coupled (or conductors there through can be electrically coupled) to one or both contacts. In FIG. 5D, various electrical components are also electrically coupled to one or more traces 310 of the printed circuit board 300 through contacts. Alternatively, the connector and other electronic components can be coupled to traces 310 at locations of the printed circuit board that do not include contacts. The components can be coupled to the printed circuit board in any suitable manner such as soldering, spot welding or the like.

Figure 6A:
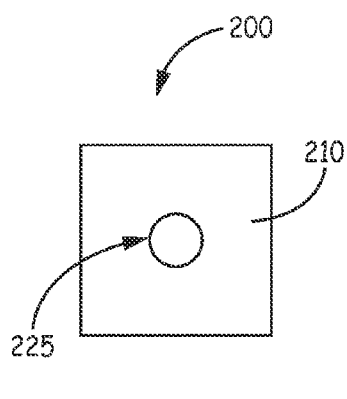
FIGS. 6A-C are schematic drawings of a front view (6A), back view (6B), and cross-sectional view (6C) of an embodiment of a connector.
Figure 6B:
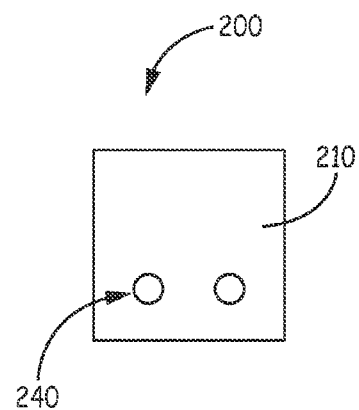
Figure 6C:
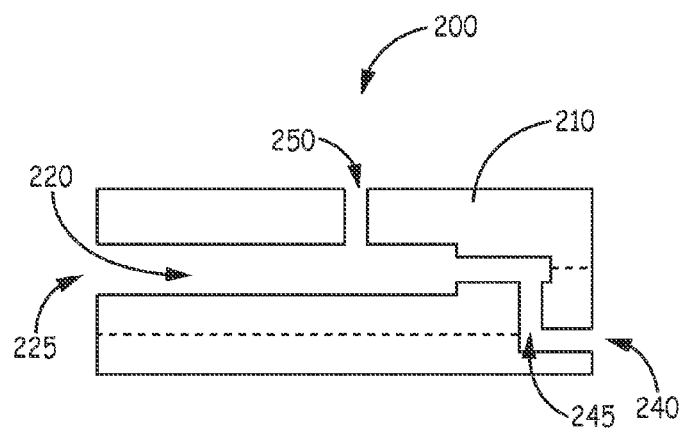

Referring now to FIGS. 6A-6C, schematic drawings of various views of an embodiment of a connector 200 are shown. FIG. 6A a front view; FIG. 68 is a back view; and FIG. 6C is a sectional view. As depicted the connector 200 includes a housing 210 that defines a lead opening 225 and a bore 220 in communication with the opening 225 and configured to receive a lead. The housing 210 also defines one or more feedthrough openings 240 (two in the depicted embodiment) and one or more feedthrough bores 245 in communication with a feedthrough opening 240. A conductor (not shown) can extend from a lead contact (not shown) disposed in lead bore 220 through feedthrough bore 245 and through opening 240 in housing 210 so that the conductor can electrically couple the lead contact to a printed circuit board. In the embodiment depicted in FIGS. 5B-C, feedthrough opening(s) 240 is depicted as being on the back of the housing 210. However, it will be understood that a feedthrough opening can be located at any suitable location of housing, such as on a side or the bottom of the housing. The location and path of the feedthrough bore 245 will be determined, at least in part, by the location of the opening 240 with which it is in communication. By way of example and with reference to FIG. 5A, if a tab 230 is conductive and configured to electrically connect to the connector to the printed circuit board, the feedthrough opening and bore defined by the housing should allow a conductor to extend through housing to the tab so that the conductor can electrically couple with the tab.

In the embodiment depicted in FIG. 6C, housing 210 defines a set screw bore 250, which can be threaded (not shown) to cooperate with threads of a set screw, extending from bore 220 to an exterior of housing 210. A set screw (not shown) can be used to retain a lead within the bore 220. It will be understood that any suitable retention mechanism can be employed to retain a lead within the bore 220.

Figure 7A:
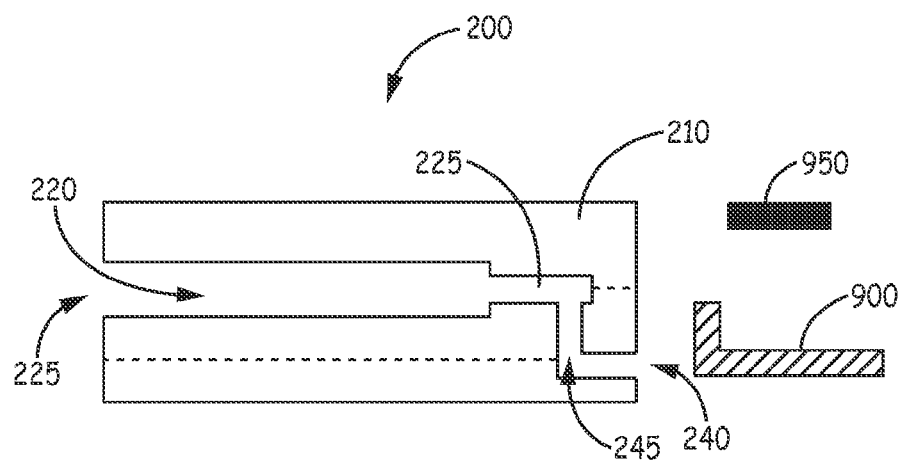
FIGS. 7A-B are schematic drawings showing a sectional view of an embodiment of a housing of a connector, a conductor, and a contact.
Figure 7B:
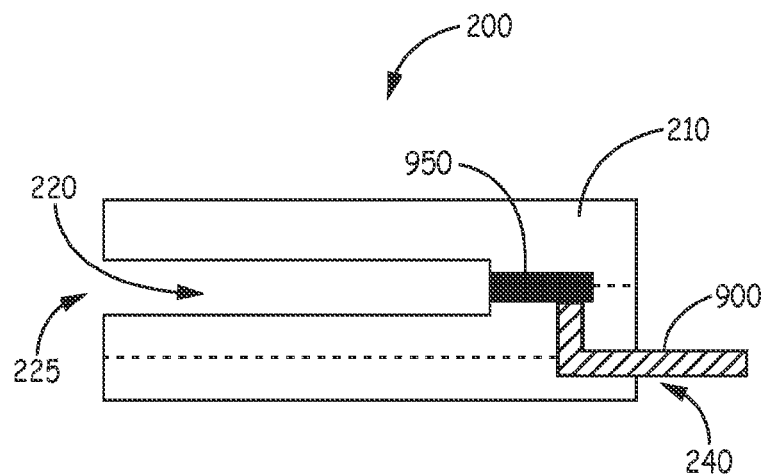

Referring now to FIGS. 7A-B, an embodiment of a housing 210, conductor 900 and contact 950 of a connector are shown. In the depicted embodiment, contact 950, which can be a cylindrical conductive element configured to receive and electrically couple with a contact of a lead (e.g., contact 610 depicted in FIG. 1), is disposed within a distal portion 225 of bore 220 defined by housing 210. The configuration of contact 950 will depend, in part, on to the configuration of the lead and a contact on the lead. In some embodiments, the lead comprises one or more ring contacts and connector 200 includes one or more canted coil spring contacts (not shown) that can serve to electrically couple with ring contacts of a lead and to mechanically retain the lead within receptacle or bore 220. In the embodiment depicted in FIGS. 7A-B, conductor 900 extends through feedthrough bore 245 and is electrically coupled to contact 950. Conductor 900 extends through feed-through opening 240 and can be electrically coupled, directly or indirectly, with a printed circuit board. In the depicted embodiment, the conductor 900 extends a distance beyond the exterior of the connector housing 210. However, in some embodiments (not shown), the conductor 900 is flush with an exterior surface of the housing 210 or is slightly recessed relative to an exterior surface of the housing 210 that defines the feedthrough opening 240. The conductor 900 can be received by feedthrough opening 240 or bore 245, or a portion thereof, by interference fit to prevent ingress of polymer during over-molding, which will be described in more detail below. Alternatively one or more insulating layers may be disposed about at least a portion of the conductor to block ingress of over-molded polymer through feedthrough bore 245 into lead bore 220. In yet another alternative, the distance between the opening 240 or the bore 245 and the conductor 900 or optional insulating layers disposed about the conductor is sufficiently large to prevent polymer ingress.

In some embodiments (not shown), conductor 900 and contact 950 are formed from a single unit.

Housing 210, conductor 900 and contact 950 can be assembled in any suitable manner, in some embodiments, the housing is formed from multiple parts. By way of example, the dashed lines in FIG. 7A represent interfaces between separate parts. Accordingly, the housing 210 depicted in FIG. 7A includes three parts. The parts can be designed to allow insertion of components (e.g., conductor 900 and contact 950) into the housing or bores of the housing (e.g., lead bore 220 and feedthrough bore 245 as the housing is assembled. The parts of the housing can be joined in any suitable manner. For example, the parts of the housing can be joined with adhesive, by welding (e.g., ultrasonic or laser welding), by snap fit, or the like.

When assembled, the housing and one or more conductors (i.e., the "housing and feedthrough assembly") is sealed relative to ingress of polymeric material into the lead bore through, for example, a seam between parts of the housing or a feedthrough bore during over-molding, in some embodiments, joined parts of the housing become sealed during the joining process. In some embodiments, the seams of the housing are configured to have a sufficiently small width or height and sufficiently large length to prevent polymer ingress during over-molding.

Figure 8:
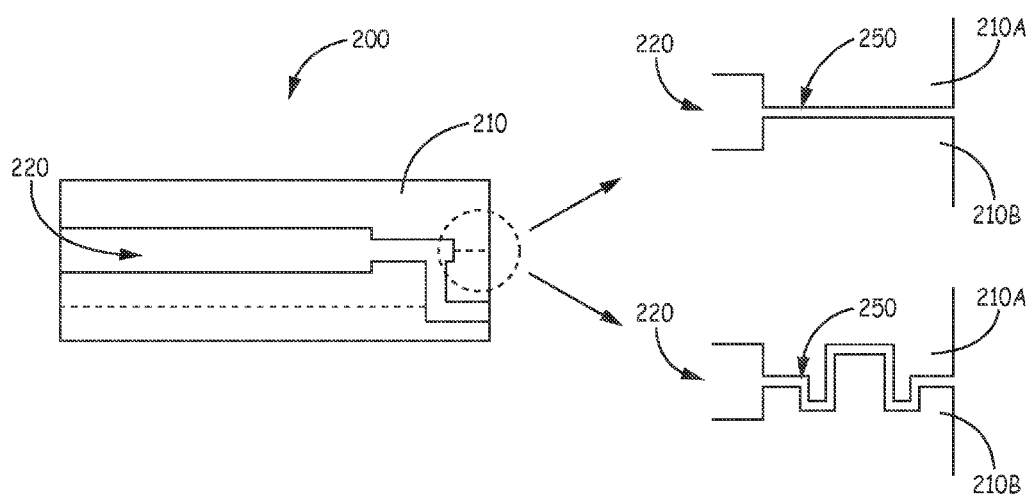
FIG. 8 shows a schematic sectional view of an embodiment of a housing of a connector and alternative seam configurations between parts of the housing.

By way of example and with reference to FIG. 8, alternative embodiments of a housing 210 of a connector 200 are shown in which a seam 250 between parts 210A, 210B of housing 210 are configured in different manners. In the top right panel, the cross-sectional shape of seam 250 between part 210A and 210B is linear. In the lower right panel, the cross-sectional shape of seam 250 between part 210A and 210B is non-linear. While the distance between parts 210A and 210B are approximately the same in the two depicted embodiments, the length between an exterior of the device and the bore 220 defined by the housing when the parts 210A, 210B are assembled is substantially longer in the embodiment depicted in the lower right panel. While the distance between the parts 210A, 210B may allow some ingress of polymer into the seam 250 during an over-molding process, the likelihood that polymer can ingress into the lead bore 220 though the seam 250 decreases as the length of the seam 250 increases from the exterior of the housing to the bore 220. Accordingly, the seam depicted in the lower right panel of FIG. 8 is more likely to prevent polymer ingress into bore 220 than the seam 250 in the upper right panel.

A housing of a connector, or parts thereof, as described herein can be formed from any suitable material. In some embodiments, the housing is formed from a polymeric material. Suitable polymeric materials for forming the connector housing, or parts thereof, include polyamide (Nylon), glass fiber filled polyamide, polyether ether ketone (PEEK), polysulfone, polyphenylene oxide, polyphenylene sulfide, liquid crystal polymer (LCP), other engineering polymers, and the like.

In some embodiments, the housing of the connector is formed from a single part. The single part can be formed through one or more molding steps. The finished product can include one or more layers of materials, in which a subsequent layer partially or fully covers one or more underlying layers.

In some embodiments, the connector is insert molded around a conductor (e.g., conductor 900 depicted in FIGS. 7A-B) and contact (e.g., contact 950 depicted in FIGS. 7A-B). A molding pin can form the lead receptacle bore of the connector and can plug the contact to prevent polymer from coating a portion of the contact that is configured to electrically couple to the lead when the lead is inserted into the bore. Alternatively, a separate piece can be used to plug the contact or to prevent one or more portions of the contact from being coated.

Once a connector as described herein is assembled and mounted to a printed circuit board, along with other mounted electronic components, which can include a battery, the printed circuit board and mounted components can be over-molded with one or more polymer to form a medical device as described herein. The over-molded polymer forms the housing of the device. The housing can be formed through one or more molding steps. The housing can include one or more layers of materials, in which a subsequent layer partially or fully covers one or more underlying layers.

The over-molding process and polymers used should be carefully selected so that one or more electronic components are not damaged during the process. In many instances a battery will be the component of the device most sensitive to heat and pressures of the molding process. Accordingly, in various embodiments, the over-molding process is performed at temperatures sufficiently low to avoid damage to a battery. In many instances, damage to a battery can occur during or following sustained temperatures of greater than about 250° C. Accordingly, in some embodiments, the molding process occurs at a temperature of below about 250° C., such as below about 235° C., below about 200° C. or below about 150° C. Any suitable polymer capable of being molded at such temperatures (i.e., having a "molding temperature" below such temperatures) can be used. Examples of suitable polymers include thermoplastic polymers such as styrene block copolymers, polyolefin blends, polyurethanes, polyamides, polyesters, polysaccharides, and copolymers and combinations thereof. Other examples include room temperature vulcanization silicon, liquid rubber silicone and the like. Other examples include polycarbonate and acrylonitrile butadiene styrene copolymer (ABS). In some embodiments, the printed circuit board and associated components is over-molded with polyamide, a thermoplastic elastomer such as styrene-ethylene-butadiene-styrene copolymer, or polyether amide.

In some embodiments, a battery-compatible polymer is employed in a first shot and a second polymer, which may or may not be battery-compatible (due to temperature), is molded over the first battery-compatible polymer. Subsequent over-molding steps with additional polymers can be employed. In some embodiments, a second or subsequent over-molded polymer imparts the housing of the device with suitable exterior properties, which may include one or more of hardness, cosmetic, toughness, color, finish, chemical compatibility (such as, for example, compatibility with isopropyl alcohol), sterilization, marking, and the like. Examples of some polymers that can impart one or more desired external qualities include those polymers listed above with regard to battery-compatibility and polyamide, thermoplastic elastomer, polyester, polyether block amide (PEBA), polyurethane, polysaccharide, polycarbonate, and acrylonitrile butadiene styrene copolymer.

The polymeric body can be over-molded by any suitable process. In some embodiments, the polymeric body is over-molded by injection molding, such as one or more of reaction-injection-molding, screw-driven injection molding, and hot-melt injection molding. Regardless of the molding process employed, a pin of plug can be inserted into the lead bore of the connector during the over-molding process to prevent polymer ingress of the over-molded polymer into the bore. In some embodiments, the polymeric body includes one or more layers or sections that are applied by way of chemical vapor deposition, which can, for example, further prevent moisture ingress.

Figure 9:
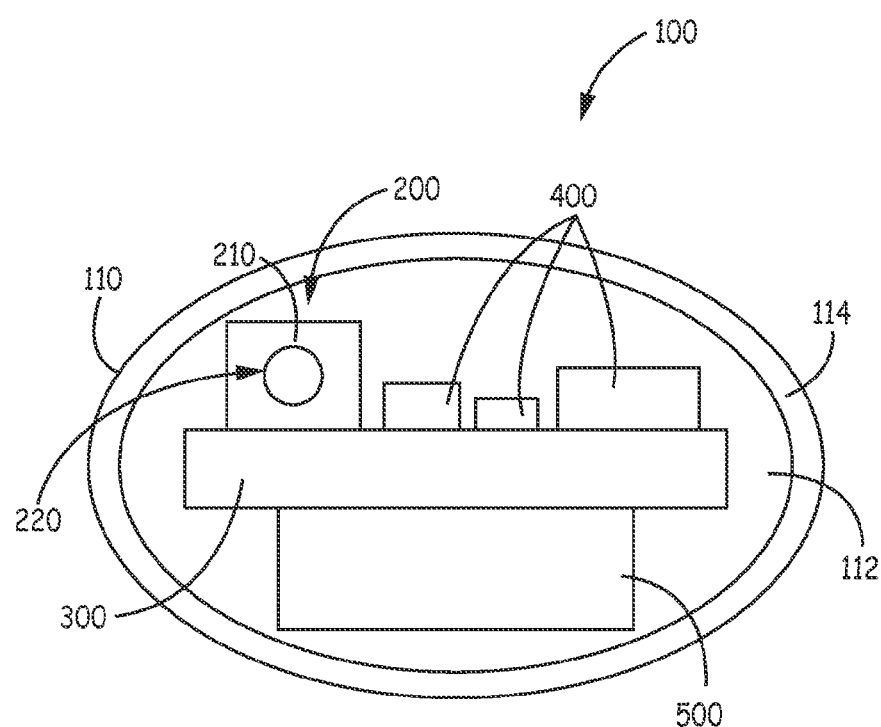
FIG. 9 is a schematic sectional view of an embodiment of a medical device.

Referring now to FIG. 9, a schematic sectional view of an embodiment of a medical device 100 is shown. The device 100 depicted in FIG. 9 is similar to the device depicted in FIG. 1. To the extent that a labeled component is not specifically discussed with regard to FIG. 9, reference is made to the discussion above regarding FIG. 1 for that component. The polymeric body 110 of the device 100 depicted in FIG. 9 includes a first polymeric layer 112 resulting from over-molding, which for purposes of the present disclosure, includes injection molding. The polymeric body 110 also includes a second polymeric layer 114 disposed over the first polymeric layer. However, it will be understood that the device body 100 can be made by any suitable numbers of layers to serve the purpose.

It will be understood that the over-molding processes described herein can be advantageously used with regard to any suitable medical device regardless of whether the device includes a lead connector. Such methods and resulting devices are contemplated herein and are within the scope and spirit of the present disclosure.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. For example "a", "an" or "the" are used to include one or more than one, independent of any other instances or usages of "at least one" or "one or more."

As used in this specification and the appended claims, the term "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising" and the like. For example, a method that "comprises" steps A, B, and C may be a method that "consists of" steps A, B and C or that "consists essentially of" steps A, B and C.

The words "preferred" and "preferably", if used herein, refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

Also herein, the recitations of numerical ranges by endpoints include all numbers subsumed within that range (e.g., 1 to 5 includes 1, 1.5, 2, 2.75, 3, 3.80, 4, 5, etc. or 10 or less includes 10, 9.4, 7.6, 5, 4.3, 2.9, 1.62, 0.3, etc.). Where a range of values is "up to" a particular value, that value is included within the range.

Thus, embodiments of MEDICAL DEVICE WITH SURFACE MOUNTED LEAD CONNECTOR are disclosed. One skilled in the art will appreciate that the articles, devices and methods described herein can be practiced with embodiments other than those disclosed. The disclosed embodiments are presented for purposes of illustration and not limitation. One will also understand that components of the devices, systems and methods depicted and described with regard the figures and embodiments herein may be interchangeable.

The above description is intended to be illustrative, and not restrictive. The above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the inventive subject matter should be determined with reference to the appended claims, along with the full scope of equivalents to which such claims are entitled.

The invention claimed is:

1. A medical device comprising:
   a printed circuit board;
   a connector configured to receive a medical lead and to electrically and mechanically couple the lead to the printed circuit board, the connector being mounted on the printed circuit board and comprising:
   (i) a housing and feedthrough assembly comprising:
      (a) a polymeric housing defining a bore configured to receive the lead, a lead opening in communication with the bore, and a feedthrough opening; and
      (b) a conductor extending through the feedthrough opening, wherein the conductor is electrically coupled with the printed circuit board,
      wherein the housing and feedthrough assembly is sealed except for the opening in communication with the bore, and
      wherein the housing and feedthrough assembly defines a non-linear seam between an exterior of the polymeric housing and the bore defined by the polymeric housing; and
   (ii) a contact disposed in the bore, electrically coupled to the conductor, and configured to electrically couple to the lead; and a polymeric body molded over the connector and the printed circuit board.

2. The medical device of claim 1, wherein the contact and the conductor comprise a contiguous electrically conductive element.

3. The medical device of claim 1, wherein the feedthrough opening is configured to receive the conductor via interference fit.

4. The medical device of claim 1, wherein the housing comprises at least two parts joined by an adhesive.

5. The medical device of claim 1, wherein the housing comprises at least two parts that together define a seam having a sufficiently small width or height and sufficiently large length to prevent the polymer of the polymer body from entering the bore of the housing through the seam when the polymer of the polymer body is over-molded over the connector.

6. The medical device of claim 1, wherein the housing is formed from a single part.

7. The medical device of claim 6, wherein the housing is molded around the conductor.

8. The medical device of claim 1, further comprising a battery operably coupled to the printed circuit board, and wherein the polymeric body is molded over the connector, printed circuit board, and the battery.

9. The medical device of claim 8, wherein the polymeric body comprises a polymer in contact with the battery, wherein the polymer in contact with the battery has a molding temperature of less than 200° C.

10. The medical device of claim 8, wherein the polymeric body comprises a polymer in contact with the battery, wherein the polymer in contact with the battery has a molding temperature of less than 250° C.

11. The medical device of claim 8, wherein the polymeric body comprises a polymer in contact with the battery, wherein the polymer in contact with the battery has a molding temperature of less than 150° C.

12. The medical device of claim 8, wherein the polymeric body comprises a polymer in contact with the battery, wherein the polymer in contact with the battery comprises polyamide, styrene-ethylene-butadiene-styrene copolymer, or polyether amide.

13. The medical device of claim 1, wherein the housing is formed from a single part molded around the conductor.

14. A connector configured to receive a medical lead and to electrically couple the lead with electronics of a medical device, the connector comprising:
  a housing and feedthrough assembly comprising:
    (a) a polymeric housing defining a bore configured to receive the lead, a lead opening in communication with the bore, and a feedthrough opening; and
    (b) a conductor extending through the feedthrough opening, wherein the conductor is configured to electrically couple to the electronics of the medical device,
    wherein, the housing and feedthrough assembly is sealed except for the opening in communication with the bore, and
    wherein the housing and feedthrough assembly defines a non-linear seam between an exterior of the polymeric housing and the bore defined by the polymeric housing; and
  a contact disposed in the bore, electrically coupled to the conductor, and configured to electrically couple to the lead.

15. The connector of claim 14, wherein the feedthrough opening is configured to receive the conductor via interference fit.

* * * * *